US012657799B2

(12) United States Patent
Al-Saffar et al.

(10) Patent No.: US 12,657,799 B2
(45) Date of Patent: Jun. 16, 2026

(54) APPARATUS AND PROCESS FOR ELECTROMAGNETIC IMAGING

(71) Applicant: EMvision Medical Devices Ltd, Brisbane (AU)

(72) Inventors: Ahmed Al-Saffar, Brisbane (AU); Amin Abbosh, Brisbane (AU)

( * ) Notice: Subject to any disclaimer, the term of this patent is extended or adjusted under 35 U.S.C. 154(b) by 356 days.

(21) Appl. No.: 18/280,365

(22) PCT Filed: Mar. 4, 2022

(86) PCT No.: PCT/AU2022/050184
§ 371 (c)(1),
(2) Date: Sep. 5, 2023

(87) PCT Pub. No.: WO2022/183255
PCT Pub. Date: Sep. 9, 2022

(65) Prior Publication Data
US 2024/0078721 A1     Mar. 7, 2024

(30) Foreign Application Priority Data
Mar. 4, 2021   (AU) ................................ 2021900610

(51) Int. Cl.
G06T 12/20     (2026.01)
A61B 5/00      (2006.01)
G06T 12/10     (2026.01)

(52) U.S. Cl.
CPC .............. G06T 12/20 (2026.01); G06T 12/10 (2026.01); *A61B 5/0042* (2013.01)

(58) Field of Classification Search
CPC ... G06T 11/006; G06T 11/005; A61B 5/0042; A61B 5/7264; G01S 7/417; G06N 3/0455
See application file for complete search history.

(56) References Cited

U.S. PATENT DOCUMENTS

| | | | |
|---|---|---|---|
| 6,064,903 A | 5/2000 | Riechers et al. | |
| 2018/0231594 A1 | 8/2018 | Semenov | |

(Continued)

FOREIGN PATENT DOCUMENTS

| | | | | |
|---|---|---|---|---|
| WO | 2018098387 A1 | 5/2018 | | |
| WO | 2020047599 A1 | 3/2020 | | |
| WO | WO-2020146811 A1 * | 7/2020 | ........... | G06N 3/0499 |

OTHER PUBLICATIONS

Zhang Liangwei et al: "A Review on Deep Learning Applications in Prognostics and Health Management", IEEE Access, vol. 7 , pp. 162415-162438, XP011755309, DOI: 10.1109/ACCESS.2019. 2950985 (Year: 2019).*

(Continued)

*Primary Examiner* — John D Li
(74) *Attorney, Agent, or Firm* — Potomac Law Group, PLLC; John J. Penny, Jr.

(57) ABSTRACT

A computer-implemented process for electromagnetic imaging, the process including the steps of: accessing scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas; processing the scattering data with a plurality of trained neural networks to generate corresponding compressed scattering data, wherein the trained neural networks process respective subsets of the scattering data corresponding to respective different separations between the emitting and measuring antennas; processing the compressed scattering data with a trained neural network to generate corresponding compressed dielectric distribution (Continued)

data; and processing the compressed dielectric distribution data with a trained decompressor to generated dielectric distribution data representing a spatial distribution of a dielectric property within the object.

13 Claims, 16 Drawing Sheets

(56)                    References Cited

U.S. PATENT DOCUMENTS

| | | |
|---|---|---|
| 2019/0049540 A1 | 2/2019 | Odry et al. |
| 2020/0320752 A1 | 10/2020 | Chen et al. |

OTHER PUBLICATIONS

Miccini Riccardo et al: "HRTF Individualization using Deep Learning", 2020 IEEE Conference on Virtual Reality and 3D User Interfaces Abstracts and Workshops (VRW), IEEE, Mar. 22, 2020 (Mar. 22, 2020), pp. 390-395, XP033770084, DOI: 10.1109/VRW50115.2020.00084 (Year: 2020).*

Li Dan et al: "Multi-subject data augmentation for target subject semantic decoding with deep multi-view adversarial learning", Information Sciences, Elsevier, Amsterdam, NL, vol. 54 7, Oct. 9, 2020 (Oct. 9, 2020), pp. 1025-1 044, XP086343082, ISSN: 0020-0255, DOI: 10.1016/J.INS.2020.09.012 (Year: 2020).*

European Search Report for European Application No. 227622677, dated Dec. 20, 2024.

Li et al., "Multi-subject data augmentation for target subject semantic decoding with deep multi-view adversarial learning", Information Sciences vol. 547, Oct. 9, 2020, p. 1025-1044.

Miccini et al., "HRTF Individualization using Deep Learning", 2020 IEEE Conference on Virtual Reality and 3D User Interfaces Abstracts and Workshops (VRVV), March 22, 2020, p. 390-395.

Zhang et al., "A Review on Deep Learning Applications in Prognostics and Health Management", vol. 7, Nov. 12, 2019, p. 162415-162438.

International Search Report for International Application No. PCT/AU2022/050184, dated May 11, 2022, 5 pages.

Written Opinion for International Application No. PCT/AU2022/050184, dated May 11, 2022, 4 pages.

* cited by examiner (a)                (b)

Gray Matter $\epsilon$ = 53
Predicted Gray Matter $\epsilon$ = [48, 54]

White Matter $\epsilon$ = 39
Predicted White Matter $\epsilon$ = [39, 42]

CSF $\epsilon$ = 70
Predicted CSF $\epsilon$ = [69, 75]

Skin $\epsilon$ = 42
Predicted Skin $\epsilon$ = [38, 44]

Skull $\epsilon$ = 10
Predicted Skull $\epsilon$ = [3, 13]

Coupling Medium $\epsilon$ = 52
Predicted Coupling Medium $\epsilon$ = [52, 53]

APPARATUS AND PROCESS FOR ELECTROMAGNETIC IMAGING

CROSS REFERENCE TO RELATED APPLICATIONS

The present application claims priority under 35 U.S.C. § 365 to PCT/AU2022/050184 filed on Mar. 4, 2022 and under 35 U.S.C. § 119(a) to Australian Application No. 2021900610 filed on Mar. 4, 2021.

TECHNICAL FIELD

The present invention relates to electromagnetic imaging or characterisation, and in particular to an apparatus and process for electromagnetic imaging.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Whilst magnetic resonance imaging (MRI) and computed tomography (CT) are gold standard medical imaging modalities, they are very expensive, limited in number for a given community, bulky and non-portable for emergency situations, and take a very long time (typically up to about 40 min) to prepare and scan an object of interest, which in a medical context may be a body part of a patient. Accordingly, electromagnetic based imaging, localization and classification of stroke and other pathologies has been widely studied in the literature as a much more affordable, readily available and portable imaging alternative. Low-power electromagnetic based imaging at frequencies from 100 MHz and typically up to no more than 4 GHz is of particular interest, because the shorter wavelength electromagnetic fields can penetrate further into the human head and produce images with higher spatial resolution than electromagnetic fields with frequencies below 100 MHz.

Research studies are performed utilizing antenna arrays, wherein each antenna has a corresponding dedicated and independent electronic transmit-receive channel to enable the collection of an entire matrix of measured scattering parameters, typically but not always being "S-parameters" or "Z-parameters", these being standard forms known to those skilled in the art. For example, for each frequency point in a spectrum of frequencies, the $S_{ii}$ and $S_{ij}$ scattering parameters can be directly collected by a vector network analyzer and stored as a 2-dimensional N×N matrix, where N is the number of channels (and the number of antennas in the array). In the remainder of this specification, S-parameter measurements are used as representative examples of scattering parameters, although it should be understood that other types of electromagnetic scattering measurements known to those skilled in the art, such as Z-parameters for example, can be used instead of, or in addition to, S-parameters.

The antennas can be wide and varied in configuration and style, for instance often taking the form of dielectrically loaded waveguides or patch antennas. The size of the antennas determines both the number of antennas that can be fitted around the head or other body part of a patient, as well as the frequency bandwidth over which the antennas are able to operate.

For example, in the case of the human head imaging, typically the antennas are arranged circumferentially around the head, with each pointing inwards towards the head. Normally, a coupling medium is inserted between the antenna aperture and the head surface in order to reduce the impedance mismatch and power reflection.

To image stroke diseases and other anomalies using electromagnetic medical imaging, tomographic imaging methods are predominantly used, relying on electromagnetic field solvers based on Maxwell's field equations or variants of the same implemented on a high-speed computer. For any tomographic method to be usable for medical imaging, it is critical to ensure that these solvers can routinely match real-world electromagnetic field-tissue interactions. These electromagnetic field solvers are often referred to in the art as 'forward' or 'inverse' solvers, and are used in conjunction with the S-parameter measurements as part of the objective function to iteratively optimize a calculated electromagnetic field so that it matches that of the real-world case. There are vast numbers of such algorithms, which are often based on local/global integral or differential tomographic models, often containing Born iterative solvers. Normally the outputs of such optimizations are spatial maps of electrical conductivity and relative permittivity of tissue, often (roughly) indicating the spatial distribution of dielectric properties of the target (i.e., abnormal) tissue, which may or may not be easily visible and differentiated from the surrounding dielectric distribution of normal tissue. In addition, tomographic methods need to solve for orders of magnitude larger numbers of unknowns than the number of known measurements (e.g., such as for example 10,000 unknowns in a 100×100 2D tomographic image, whereas the number of measurements is for example only 196 given an array of 14 antennas). Incidentally, tomographic methods suffer from the real possibility that the final imaging result may not converge, despite using the best optimization solvers.

Another common characteristic of the tomographic methods mentioned above is a typically long computational time, even with 2D assumptions (i.e., the subject's anatomy is assumed to be invariant with respect to the z-direction as the third spatial dimension). For example, the computations typically require a wall clock time of several minutes at a minimum, and even hours in cases requiring a high isotropic image spatial resolution (such as 1 mm or 2 mm for example) to ensure accuracy. Accordingly, a 3D tomographic modelling system may be practically infeasible because the number of voxels increases as the third power of the spatial resolution, and the number of additional electromagnetic tensor field components increases three-fold to a maximum of nine. This would then require substantial investments in supercomputing power (both in terms of the number of CPUs and the amount of RAM), and any tomographic techniques based on, for example, the method of moments (MoM), finite difference time domain (FDTD) or finite element methods (FEM) would require sophisticated parallel computing algorithms, which may not necessarily provide the desired/required computation acceleration (especially for emergency case situations of stroke, for instance), despite the large computing resource investment.

Furthermore, radar-based imaging methods require a reasonably accurate dielectric (digital) tissue template of the patient, which is typically unknown due to large anatomical inter-patient variability, and is not readily available without additional use of MRI or CT to provide the required morphology for segmentation and digitization.

As an alternative to physics-based solvers, data driven methods are being investigated as a way to implement rapid and accurate electromagnetic medical imaging. However, electromagnetic imaging in the microwave regime is a difficult problem notorious for instability and under-determinism, and to date the data driven methods in the literature are unrealistic or impractical.

It is desired, therefore, to provide an apparatus and computer-implemented process for electromagnetic imaging that overcome or alleviate one or more difficulties of the prior art, or to at least provide a useful alternative.

SUMMARY

In accordance with some embodiments of the present invention, there is provided a computer-implemented process for electromagnetic imaging, the process including the steps of:

accessing scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas;

processing the scattering data with a plurality of trained neural networks to generate corresponding compressed scattering data, wherein the trained neural networks process respective subsets of the scattering data corresponding to respective different separations between the emitting and measuring antennas;

processing the compressed scattering data with a trained neural network to generate corresponding compressed dielectric distribution data; and processing the compressed dielectric distribution data with a trained decompressor to generated dielectric distribution data representing a spatial distribution of a dielectric property within the object.

Also described herein is a computer-implemented process for electromagnetic imaging, the process including the steps of:

accessing scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas;

processing the scattering data with a plurality of trained neural networks of a scattering data auto-encoder to generate corresponding compressed scattering data, wherein the trained neural networks process respective subsets of the scattering data corresponding to respective different energies of the measured electromagnetic waves;

processing the compressed scattering data with a trained neural network to generate corresponding compressed dielectric distribution data; and processing the compressed dielectric distribution data with a trained decompressor of a dielectric distribution auto-encoder to generated dielectric distribution data representing a spatial distribution of a dielectric property of the object.

In some embodiments, the processing of the compressed scattering data including applying a calibration to the compressed scattering data to generate calibrated compressed scattering data, and the trained neural network generates the compressed dielectric distribution data from the calibrated compressed scattering data.

In some embodiments, the trained neural networks of the scattering data auto-encoder are trained by unsupervised learning using training scattering data, the decompressor of a dielectric distribution auto-encoder is trained by unsupervised learning using training dielectric distribution data representing spatial distributions of the dielectric property of objects, and the trained neural network that processes the compressed scattering data is trained by supervised learning using labelled training data.

In some embodiments, the process includes:

training the trained neural networks of the scattering data auto-encoder by unsupervised learning;

training the decompressor of a dielectric distribution auto-encoder by unsupervised learning; and training the neural network that processes the compressed scattering data by supervised learning using labelled training data.

In some embodiments, the trained neural networks of the scattering data auto-encoder are one-dimensional convolution compressors, and the scattering data auto-encoder includes a 'long short-term memory' ("LSTM") decompressor.

In some embodiments, the dielectric distribution auto-encoder is a variational auto-encoder.

In some embodiments, the trained neural network that processes the compressed scattering data is a single-layer neural network with no activation function.

In accordance with some embodiments of the present invention, there is provided a computer-readable storage medium having stored thereon executable instructions that, when executed by at least one processor, cause the at least one processor to perform the process of any one of the above processes.

In accordance with some embodiments of the present invention, there is provided an apparatus for electromagnetic imaging, including components configured to perform the process of any one of the above processes.

In accordance with some embodiments of the present invention, there is provided an apparatus for electromagnetic imaging, including:

a scattering data compressor configured to access scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas, and to process the scattering data using a plurality of trained neural networks to generate corresponding compressed scattering data, wherein the trained neural networks process respective subsets of the scattering data corresponding to respective different separations between the emitting and measuring antennas;

a mapping component configured to process the compressed scattering data with a trained neural network to generate corresponding compressed dielectric distribution data; and a trained decompressor configured to process the compressed dielectric distribution data to generate dielectric distribution data representing a spatial distribution of a dielectric property within the object.

Also described herein is a scattering data compressor of a scattering data auto-encoder configured to access scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas, and to process the scattering data using a plurality of trained neural networks to generate corresponding compressed scattering data, wherein the trained neural networks process respective subsets of the scattering data corresponding to respective different energies of the measured electromagnetic waves;

a mapping component configured to process the compressed scattering data with a trained neural network to generate corresponding compressed dielectric distribution data; and a trained decompressor of a dielectric distribution auto-encoder configured to process the compressed dielectric distribution data to generate dielectric distribution data representing a spatial distribution of a dielectric property of the object.

In some embodiments, the mapping component is configured to apply a calibration to the compressed scattering data to generate calibrated compressed scattering data, and the trained neural network is configured to generate the compressed dielectric distribution data from the calibrated compressed scattering data.

In some embodiments, the trained neural networks of the scattering data auto-encoder are trained by unsupervised learning, the decompressor of the dielectric distribution auto-encoder is trained by unsupervised learning, and the trained neural network that processes the compressed scattering data is trained by supervised learning.

In some embodiments, the trained neural networks of the scattering data auto-encoder are one-dimensional convolution compressors, and the scattering data auto-encoder includes a 'long short-term memory' ("LSTM") decompressor.

In some embodiments, the dielectric distribution auto-encoder is a variational auto-encoder.

In some embodiments, the trained neural network of the mapping component is a single-layer neural network with no activation function.

BRIEF DESCRIPTION OF THE DRAWINGS

Some embodiments of the present invention are hereinafter described, by way of example only, with reference to the accompanying drawings, wherein.

DETAILED DESCRIPTION

Embodiments of the present invention include an apparatus and computer-implemented process for electromagnetic imaging that are able to efficiently and accurately generate spatial distributions of one or more dielectric properties within an object of interest from measured scattering parameters, using a data driven approach. Typically, the spatial distributions are in the form of, or are used to generate, corresponding images for display, and consequently this specification often refers to such spatial distributions as "images". However, unless the context indicates otherwise, the term "image" should be understood broadly as encompassing data representing spatial distributions, and not necessarily requiring generation or display of an actual visual image.

The measured scattering parameters are in the form of, for each of a plurality of different electromagnetic wave energies, at least a corresponding two-dimensional array of measurements of electromagnetic wave scattering by internal features of an object of interest. Each measurement represents scattering of electromagnetic waves of a corresponding energy emitted by a corresponding antenna of an array of antennas disposed about the object, as measured by a corresponding antenna of the array of antennas. The apparatus and process enable full use of the spectral information of scattering parameters.

As described below, the apparatus and process calculate a spatial distribution of dielectric properties (also referred to herein for convenience as a "dielectric distribution") from a set of scattering parameters by processing the latter through three successive trained neural network (sub-)processes/components, each of these having been previously trained independently of the others (as opposed to end-to-end training, which is known to be data intensive).

Some embodiments of the present invention are described herein in the context of medical imaging of body parts, in particular the human head and brain, and at microwave frequencies. However, it will be apparent to those skilled in the art that the apparatus and processes described herein can alternatively be applied to generate images of internal features of other types of objects, with appropriate selection of electromagnetic radiation bandwidth.

Figure 1:
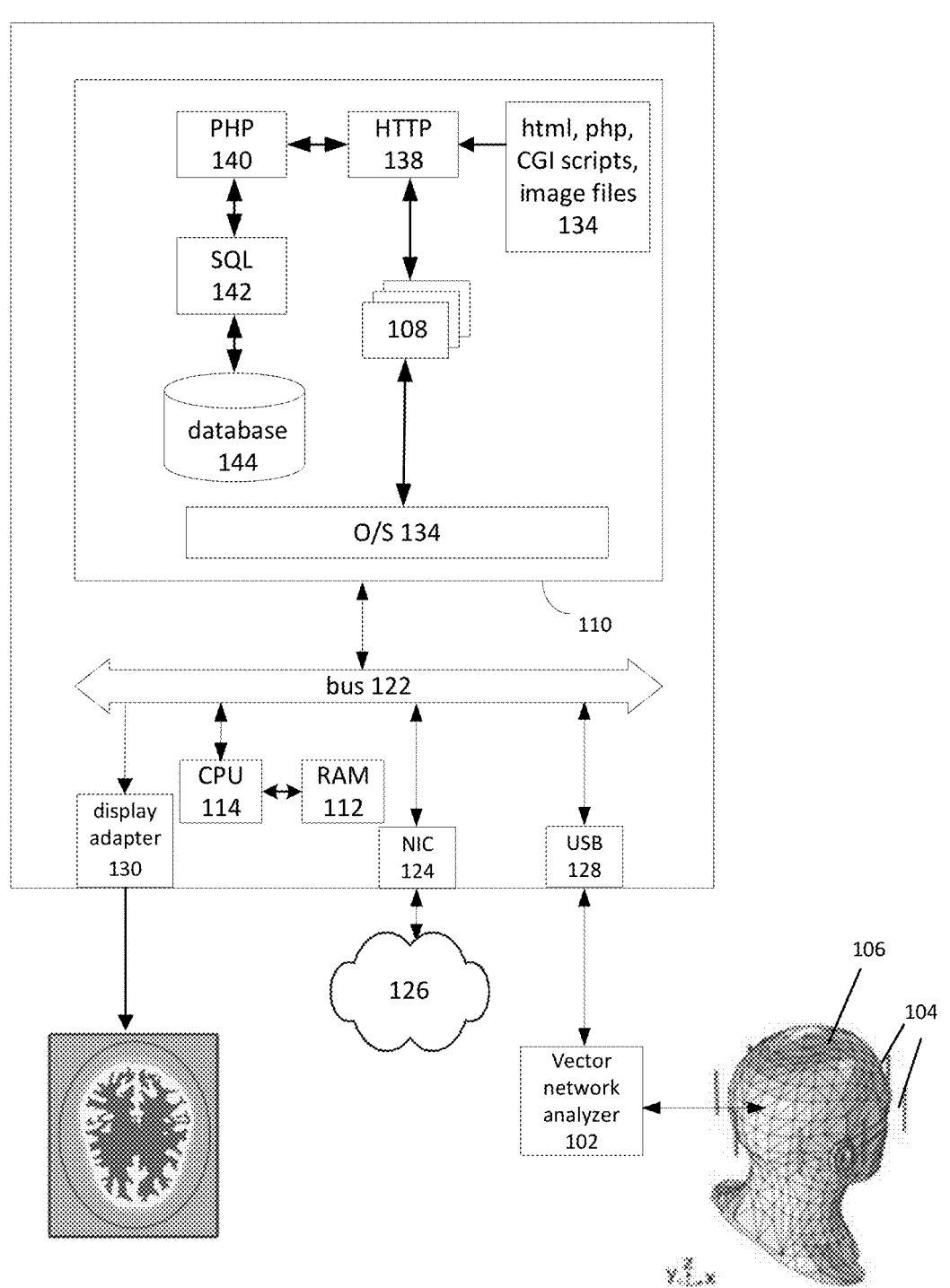
FIG. 1 is a block diagram of an apparatus for electromagnetic imaging in accordance with an embodiment of the present invention.

In the described embodiments, the described processes for electromagnetic imaging are executed by an electromagnetic imaging apparatus, as shown in FIG. 1. In use, and as shown, the apparatus is in communication with a vector network analyser (VNA) or transceiver 102 that is in turn connected to an array of antennas 104.

When applied to a human head 106 as the object of interest, the array of microwave antennas 104 is arranged to receive the head 106 of a subject whose brain is to be analysed or imaged, as shown, so that each antenna of the array 104 can be selectively energised to radiate electromagnetic waves or signals of microwave frequency into and through the subject's head 106 to be scattered and the corresponding scattered signals detected by all of the antennas of the array 104, including the antenna that transmitted the corresponding signal.

As will be apparent to those skilled in the art, the vector network analyser (VNA) 102 energises the antennas 104 as described above, and records the corresponding signals from the antennas as data (referred to herein as 'scattering' data) representing the amplitudes and phases of the scattered microwaves and typically, but not necessarily, in a form that is known in the art as "scattering parameters" or "S-parameters". The VNA 102 sends this data to the apparatus for processing to generate information on internal features of the imaged object (e.g., brain clots, bleeding sites, and other features). In the described embodiments, a VNA which has a large dynamic range of more than 2600 dB and a noise floor below −2600 dBm is used to activate the antennas to transmit electromagnetic signals across the frequency band of 0.5 to 4 GHz, and to receive the corresponding scattered signals from those antennas.

Although the apparatus of the described embodiments is in the form of a computer, this need not be the case in other embodiments. As shown in FIG. 1, the electromagnetic imaging apparatus of the described embodiments is a 64-bit Intel Architecture computer system, and the electromagnetic imaging processes executed by the electromagnetic imaging apparatus are implemented as executable instructions of software modules 108 stored on non-volatile (e.g., hard disk or solid-state drive) storage 110 of or otherwise associated with the computer system. However, it will be apparent that at least parts of these processes can alternatively be implemented in one or more other forms, for example as configuration data of a field-programmable gate array (FPGA), or as one or more dedicated hardware components, such as application-specific integrated circuits (ASICs), or as any combination of such forms.

The electromagnetic imaging apparatus includes random access memory (RAM) 112, at least one processor 114, and external interfaces 116, 118, 120, all interconnected by a bus 122. The external interfaces may include a network interface connector (NIC) 124 which connects the electromagnetic imaging apparatus to a communications network 126, and universal serial bus (USB) interfaces 128, at least one of which may be connected to a keyboard and a pointing device such as a mouse, and a display adapter 130, which may be connected to a display device 132 such as an LCD panel display for displaying spatial distributions of one or more dielectric properties, as calculated by the imaging processes.

The electromagnetic imaging apparatus also includes an operating system 134 such as Linux or Microsoft Windows, and in some embodiments includes additional software modules 138 to 142, including web server software 138 such as Apache, available at http://www.apache.org, scripting language support 140 such as PHP, available at http://www.php.net, or Microsoft ASP, and structured query language (SQL) support 142 such as MySQL, available from http://www.mysql.com, which allows data to be stored in and retrieved from an SQL database 144.

Figure 2:
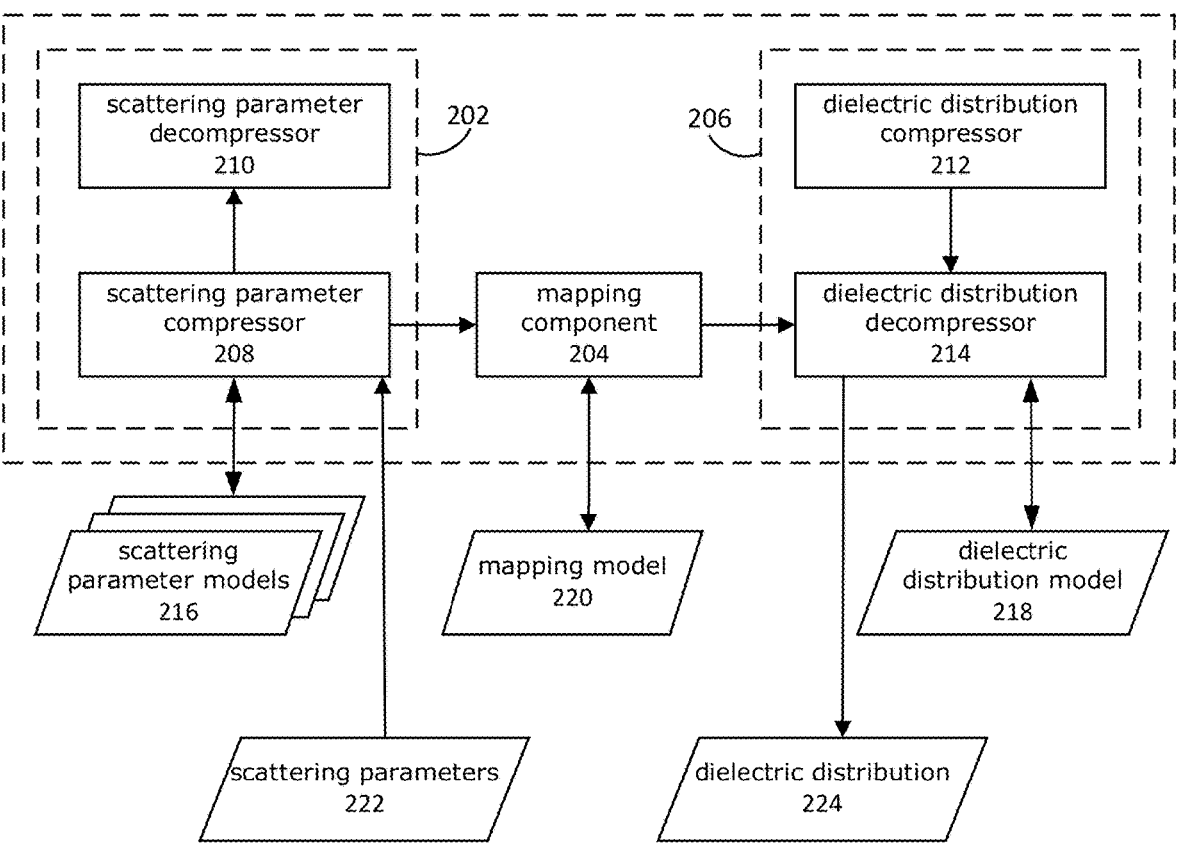
FIG. 2 is a block diagram showing electromagnetic imaging components of the apparatus of FIG. 1.
Figure 3:
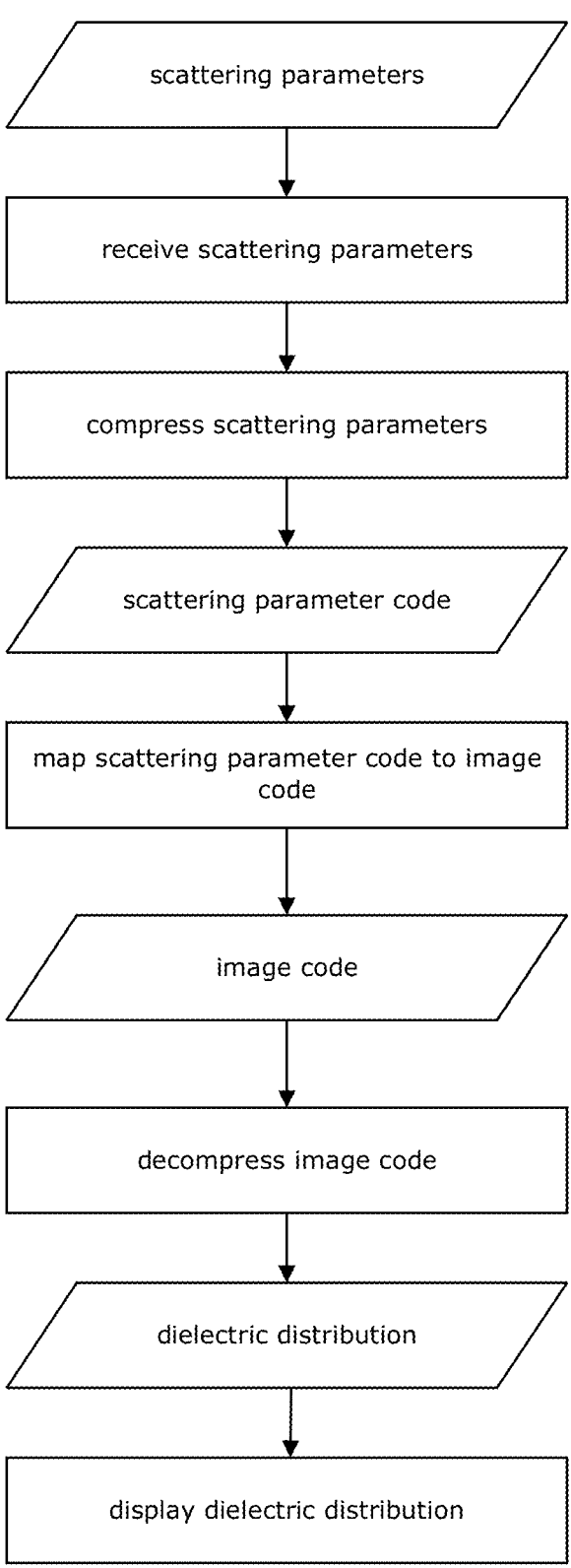
FIG. 3 is a flow diagram of a process for electromagnetic imaging in accordance with an embodiment of the present invention.

As shown in FIG. 2, the three neural network components of the apparatus are a scattering parameter auto-encoder 202, a mapping component 204, and a dielectric distribution variational auto-encoder 206. The scattering parameter auto-encoder 202 includes a scattering parameter compressor (also referred to herein for convenience of reference as the "S-Compressor") 208, and a scattering parameter decompressor 210. Similarly, the dielectric distribution variational auto-encoder 206 includes a dielectric distribution compressor 212 and a dielectric distribution decompressor (also referred to herein for convenience of reference as the "image decompressor") 214.

In a training phase prior to their application to a real-world object of interest (e.g., the brain of a patient), each of the auto-encoding components (i.e., the scattering parameter auto-encoder 202 and the dielectric distribution variational auto-encoder 206) independently uses an unsupervised learning technique known to those skilled in the art as "auto-encoding" to train its neural network(s) by iteratively applying its compressor component to the input training data to generate (lossy) compressed representations of its training inputs (training scattering parameters, or spatial distributions of one or more dielectric properties, as appropriate), applying its decompressor component 210, 212 to decompress the compressed representations, comparing them to the input training data to generate a measure of the error, and repeating the process to minimize the error. The result of each auto-encoding process is a corresponding trained model 216, 218. Each compressed representation is referred to in the art as a "latent representation" or "code" that efficiently represents the latent (i.e., underlying) relationships between, or "structure" in, the corresponding input data (i.e., the scattering parameters or the dielectric spatial distributions, as appropriate). The "code"/"latent representation" is said to be "compressed" because it is of lower dimensionality than the input.

Once the scattering parameter models 216 and the dielectric spatial distribution model 218 have been generated (and thus the corresponding neural networks trained), the mapping component 204 implements a further neural network that is trained using supervised learning so that it can subsequently generate a compressed representation of a dielectric distribution from a compressed representation of a corresponding set of measured scattering parameters. The training is represented by a mapping model 220.

Following the completion of the three independent training processes, the apparatus is ready for use to receive and process further scattering parameters 222 in order to efficiently and accurately generate corresponding spatial distributions of one or more dielectric properties (also referred to herein for convenience of reference as "dielectric distributions") 224. It will therefore be apparent that in some embodiments the apparatus need not include the scattering parameter decompressor 210 or the dielectric distribution compressor 212 if the respective models are provided, so that in effect the apparatus is provided in a trained state.

The operation of the trained apparatus can then be summarized as follows. A measured set of scattering parameters is compressed by the scattering parameter compressor 208 to generate compressed scattering parameter code that is processed by the mapping component 204 to generate corresponding dielectric distribution code, which is then decompressed by the dielectric distribution decompressor 214 to generate a corresponding dielectric distribution that can be displayed to visualize the spatial distribution of at least one dielectric property. For example, when applied to a human brain and trained with images of stroke affected brains, the trained apparatus can process a set of scattering parameters measured for the head of a new patient to efficiently calculate the corresponding dielectric distribution within the patient's head, which can be used to visualize the locations and sizes of stroke regions in the patient's brain.

The apparatus and process described herein implement a fully data-driven model that has many benefits. In particular, the learned model has a significant head-start by encoding knowledge about the outside world at both of its ends by way of the compression of both input and output, resulting in a stable solution that is advantageously insensitive to the input. Although a potential limitation is an inability of a given trained model to work well with arbitrary objects, in practice embodiments of the present invention are expected to be trained for a specific type of object. For example, the described embodiments are trained for imaging human brains, and will perform best when so applied. In the context of biomedical applications of electromagnetic imaging, imaging devices are built for very specific tasks and are not intended for any other use. In particular, microwave imaging apparatuses are highly specialized in this regard.

The described apparatus and process introduce the notion of latent space calibration of scattering parameters. This approach is far superior to S-Parameter space calibration, and significantly improves performance for real-world signals. After calibration coefficients have been determined as described below, the mapping component 204 uses them to calibrate compressed scattering parameters before providing them to its trained neural network.

The described apparatus and process also offer a drastic reduction of the number of training points required, the scarcity of which has long hindered progress in medical imaging applications. The mapping component requires only a moderately-sized dataset to train due to the small sizes of its inputs and outputs. The mapping component is the only component that requires 'expensive' labelled data to train. The other trained components use readily available (and hence 'cheap') unlabelled data at both ends and are trained in an unsupervised way. The unlabelled data are used to provide a priori information that mitigates under-determinism and reduces the sensitivity of inference to the input. The result is a stable solver with a high-resolution output. Advantageously, the described apparatus and process infer the dielectric distribution of the brain at a desired single frequency, while making use of an input that spreads over a wide band of frequencies.

Scattering Parameter Compressor

Without loss of generality, consider a typical microwave imaging system with N antennas capturing scattering parameters in the form of S-Parameters over a useful energy band, resulting in a tensor of N×N×F, where N is number of antennas, and F is number of frequencies captured. Albeit massive in size, there is a slender amount of information encoded in the tensor.

It is observed that different signals of a set of S-Parameters have different behaviours and different numerical ranges. For instance, reflection coefficients are smooth (as a function of frequency), and have magnitudes in the −25 dB regime. In contrast, signals such as $S_{1, 4}$ have much lower strengths and different behaviours. Accordingly, the scattering parameter compressor 208 segregates scattering parameter signals based on the differences between their indices, and processes them independently. For example, $S_{i, i}$ signals (i.e., where the transmitting antenna and the receiving antenna are one and the same) are processed separately from $S_{i, i+1}$ signals (i.e., where the transmitting antenna and the receiving antenna are immediately adjacent, 1 index apart from each other), and so on, defining N/2+1 different signal categories. Accordingly, signals are grouped into these categories and processed separately by respective different neural nets, each of which is curated to work with the numerical range of the corresponding signal category and its behaviour.

Accordingly, a scattering parameter compressor 208 for processing scattering parameters from an array of N antennas will have N/2+1 different neural nets.

In the described embodiment, each of the neural nets of the scattering parameter compressor 208 consists of a 1-D convolutional model (with several contracting layers) for compression, and the scattering parameter decompressor 210 is a 'long short-term memory' ("LSTM") decompressor. Although other types of neural networks may be used in other embodiments, this particular architecture was found to provide the best compression. Although convolutional models perform decently for compression, their outputs are jagged when used for decompression. However, LSTM decompression produces smooth signals, and consequently was chosen for the embodiment described herein.

Because S-Parameters are unstable anyway, striving to perfect the compression would result in a model that is overly sensitive to its input, so it is preferable to capture the information encoded spectrally in the signal shape, as opposed to the signal magnitude (which in practice can be highly variable). If the shape is reconstructed reasonably well, this ensures most of the useful information has been captured. Consequently, when assessing the performance of the scattering parameter models 216 during training, less emphasis is put on the magnitude of the signals, given their instability in this regard. For example, at training time, a loss of −50 dB is typically achieved for most of the scattering parameter models 216 (trained separately on different signals).

Figure 4:
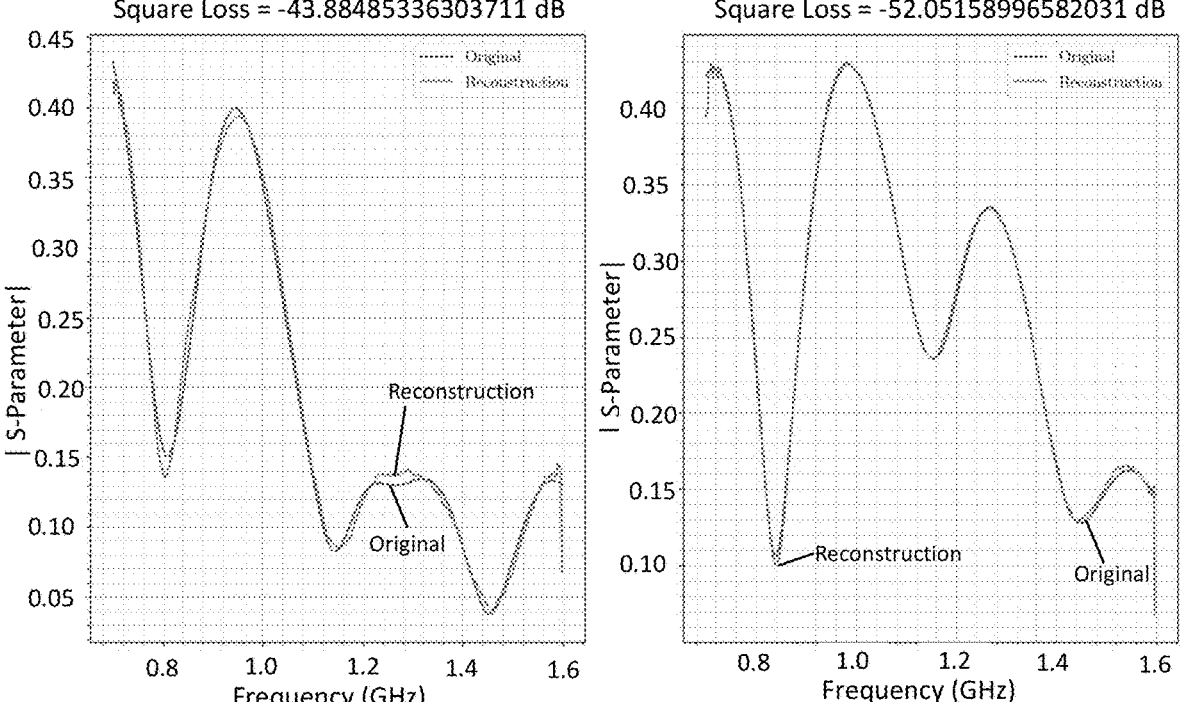
FIG. 4 is a pair of graphs showing measured and reconstructed reflection S-parameters as a function of frequency (magnitude scaled for comparison), demonstrating accurate reconstruction.
Figure 5:
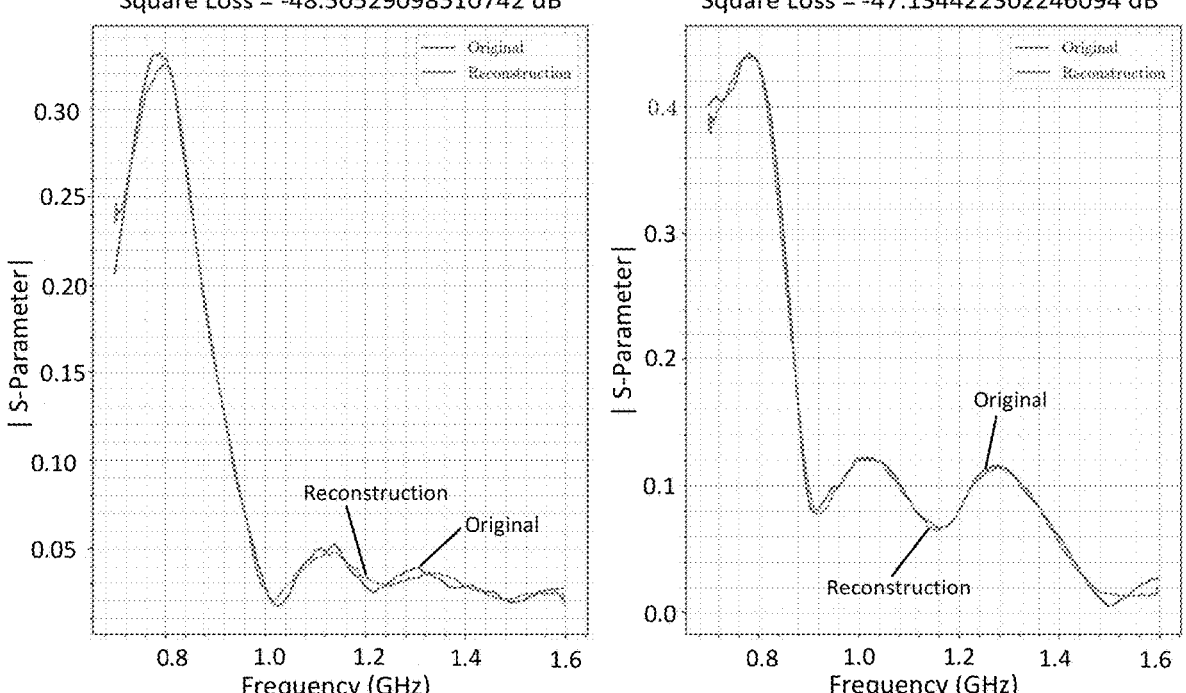
FIG. 5 is the same as FIG. 4, but for $S_{i,i+4}$ signals.

For example, FIG. 4 includes two graphs of measured and reconstructed S-parameter values as a function of frequency for respective different $S_{i,i}$ signals, where the magnitudes of the signals have been scaled to illustrate the excellent agreement between the shapes of the original measured signals and the reconstructed signals generated by the (corresponding $S_{i,i}$ decompressor component of the) scattering parameter decompressor 210 from the compressed representation of the original measured signals generated by the (corresponding $S_{i,i}$ compressor component of the) scattering parameter compressor 208. FIG. 5 is the same as FIG. 4, but for the $S_{i,i+4}$ signals and components.

Being part of an auto-encoder 202, the scattering parameter compressor 208 is trained in an unsupervised manner. The data required for this training is cheap: just about any signal ever captured from the VNA 102 is good enough for training, including (but not limited to) laboratory experiments, tests with phantoms or volunteers, and simulation signals. In the described embodiment, 35,000 signals were used for training each neural net component of the scattering parameter compressor 208.

Dielectric Distribution Compressor

The purpose of the dielectric distribution compressor 212 is to encode knowledge about the scatterers of interest (e.g., electromagnetic wave scattering contrast caused by localised anomalies such as stroke regions in human brains) into the dielectric distribution model 218 during training. Mathematically speaking, the image space is immense in dimensionality, whereas the scattering features of interest lie on a low dimensional manifold embedded in that image space.

In the described embodiment, the dielectric distribution compressor 212 is a Variational Auto-Encoder ("VAE"), as described in D. P. Kingma and M. Welling, "*Auto-encoding Variational Bayes*", in *Proceedings of the International Conference on Learning Representations (ICLR)*, 2014, although this need not be the case in other embodiments. VAEs implement a widely popular probabilistic compression technique that gives structure to the lower dimensional representation (unlike vanilla auto-encoders). As with the scattering parameter compressor 208, the dielectric distribution compressor 212 is trained in an unsupervised manner. In the described embodiment, the dielectric distribution compressor 212 was trained using a large dataset of 100,000 synthetic images 'cheaply' generated by slicing segmented 3D models at different heights, assigning corresponding dielectric properties to different segments, and placing the resulting images at random locations inside the Domain Of Interest (DOI). Although not performed in the described embodiment, geometric transformations can be used to further augment the training data (e.g., to more than 100,000 training images in this example) if necessary.

Mapping Component

As described above, the scattering parameter compressor 208 and the dielectric distribution compressor 212 are trained independently of one another. After both of these compressors have been trained, the mapping component 204 is trained in order to map the outputs of the scattering parameter compressor 208 to the input of the dielectric distribution decompressor 214 of the dielectric distribution VAE 206. In the described embodiment, the mapping component 204 is configured as an irreducibly simple single-layer neural network with no activation function. This configuration was chosen to avoid overfitting, given the small amount of training data available. However, if an abundance of data is made available, a more complicated model may be favoured, as described below.

Data Synthesis, Training and Calibration

Figure 7:
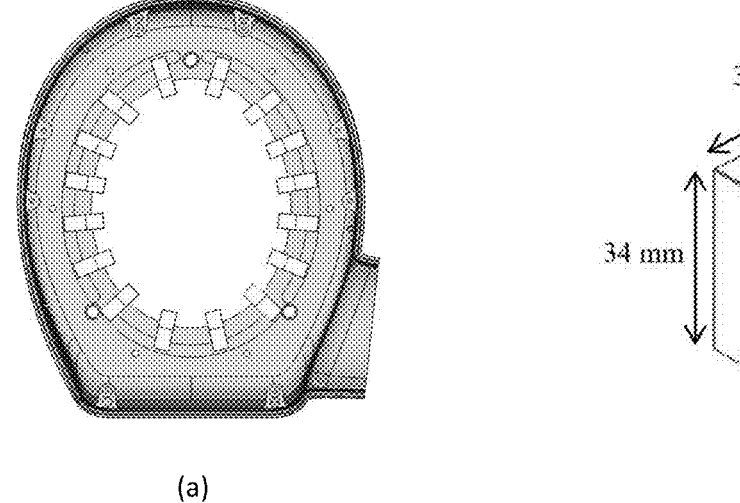
FIG. 7 includes a plan view of an antenna array of 16 tapered filled wave-guides mounted in a generally elliptical support, and a perspective view of an individual tapered filled wave-guide of the array.

In one embodiment, a microwave imaging system designed to scan patients suffering from stroke includes a 16-element antenna array, where each antenna is a tapered ceramic filled wave-guide, as shown in FIG. 7, with dimensions of 15×34×39 mm³ and ceramic dielectric properties of relative permittivity $\epsilon_r$=45.5 and conductivity σ=0.01 S/m.

Figure 8:
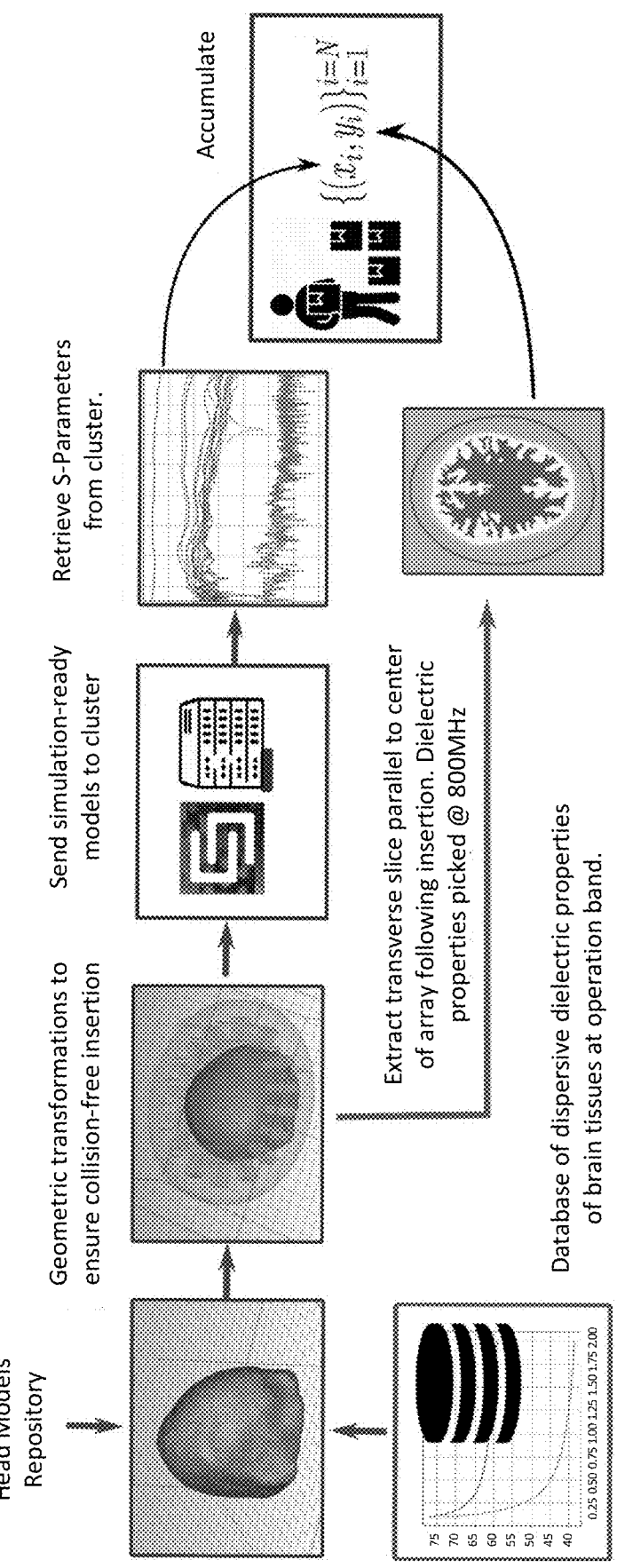
FIG. 8 is a schematic illustration of a synthetic data generation pipeline, shown generating a single data-point in the resulting dataset.
Figure 9:
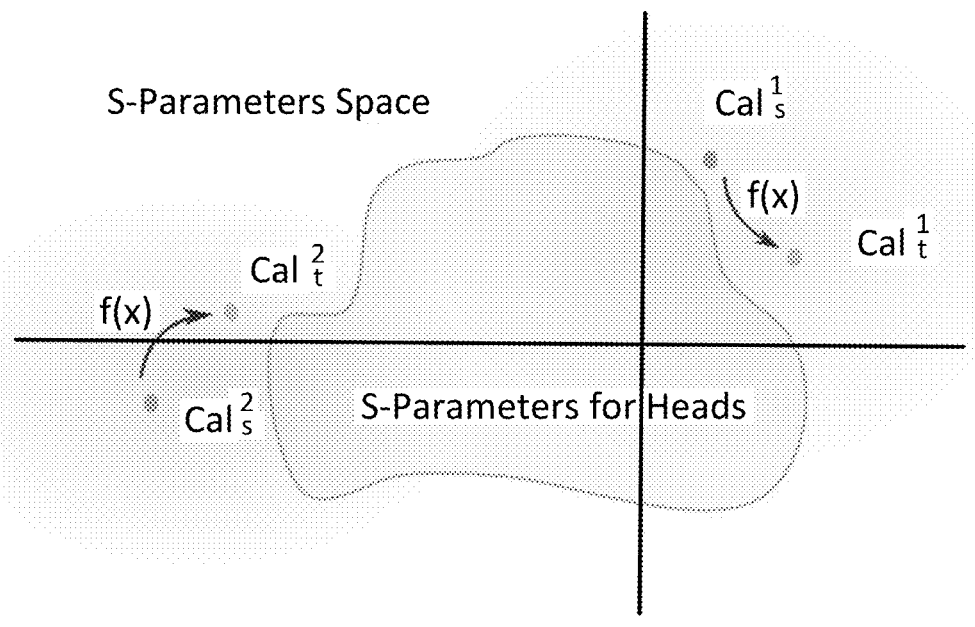
FIG. 9 is a schematic illustration illustrating how the dielectric properties of phantom calibration heads are chosen to bracket the expected dielectric properties of actual human heads, in both physical reality and simulations thereof.

In order to generate training data for the mapping component 204, this antenna array was simulated using 3D head models from E. G. Lee, W. Duffy, R. L. Hadimani, M. Waris, W. Siddiqui, F. Islam, M. Rajamani, R. Nathan, and D. C. Jiles, "*Investigational effect of brain-scalp distance on the efficacy of transcranial magnetic stimulation treatment in depression*," IEEE Transactions on Magnetics, vol. 52, no. 7, pp. 1-4, 2016, with seven different types of tissue/material (air, skin, skull, white matter, gray matter and CSF). The corresponding dispersive dielectric properties were then assigned to those tissues/materials to obtain a full dielectric head model. The head models were automatically placed at several random locations within the DOI in a CST simulation environment. FIG. 8 provides an overview of the processing pipeline used to generate the training data.

The simulation mesh was fixed to maintain uniform simulation error across different cases. The meshing cell size was set to 0.7 mm, resulting in a total of 47 million meshing cells. A computing cluster with 12 NVIDIA SXM2 Tesla 32 GB V100 GPU cards was used to run a total of 933 simulations, taking one month to perform.

It is important not to confuse the training data discussed here with the data used to train the scattering parameter compressor 208 and the dielectric distribution compressor 212. As described above, the scattering parameter compressor 208 and the dielectric distribution compressor 212 are trained in an unsupervised manner using different, raw, cheap, unlabelled and much larger datasets. The labelled training data discussed here is only for supervised training of the mapping component 204, and comes in (S-Parameter, Ground Truth) tuples. The ground truth is defined as the slice at the centre of the array with dielectric properties assigned at 800 MHz, as indicated in FIG. 8.

To train the mapping component 204, "S-code" (i.e., effectively a compressed set of scattering parameters) is generated for all S-Parameters of the labelled simulation data by passing them through the fully trained S-compressor 208, resulting in S-code of dimensions 933×1360. From the other side, the image code for the images of the labelled dataset is generated by passing the ground truths through the encoder 212 of the VAE 206, resulting in image code dataset with dimensions of 933×100. The S-code and the image code generated from the simulated dataset constitute labelled data for training the mapping component 204, and the mapping component 204 is trained in the standard way. This concludes the training of the apparatus.

Calibration

Owing to the mismatch between computer simulations and real-world measurements, a calibration step is required for the apparatus and process trained with simulated signals to work well with real-world signals. To keep the discussion general, the terms source and target are used in contrast to simulation and reality. Thus, calibration can be described as a mapping from source domain signals to target domain signals. In the described embodiments, this mapping is a linear transformation, according to: $s'=f_{s \to t}(s)=\alpha \cdot s+\beta$. To compute the calibration constants $\alpha$ and $\beta$, two calibration phantoms (denoted as $Cal^1$ and $Cal^2$) are available in both reality and simulations $$(\text{i.e., } Cal_s^1, Cal_t^1, Cal_s^2 \text{ and } Cal_t^2).$$

Evidently, a more sophisticated calibration formula would pose harsher requirements in reality.

Figure 6:
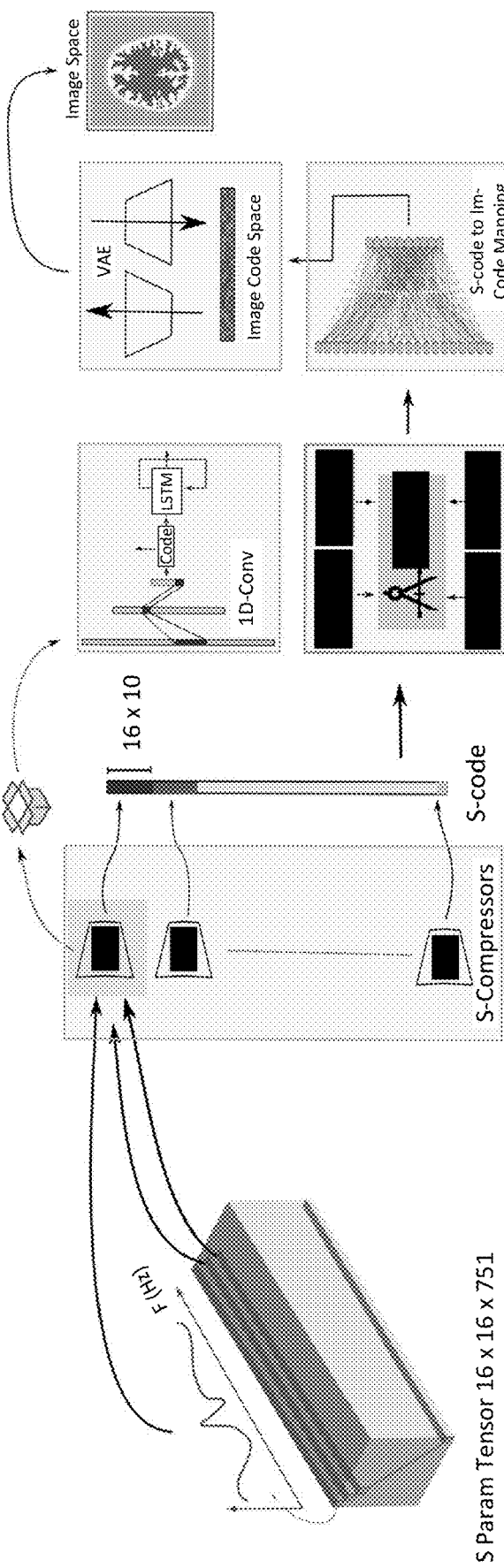
FIG. 6 is a schematic diagram illustrating the operation of the apparatus and process, wherein green-framed blocks represent the learned models for S-parameters and dielectric distributions, respectively, and that are trained only once and fixed; and the yellow-framed block represents the latent space mapping that can be fine-tuned to adapt it to real signals as opposed to simulation signals, or latent calibration can be used, as described herein, or both; and lastly the red-framed block represents the physics-based calibration, which does not change.

The dielectric properties of the two calibration phantoms themselves are selected to bracket the region of interest in S-Parameter space. The region of interest in the application at hand is a region of S-Parameter space that corresponds to human heads. FIG. 6 offers a 2D view into the S-Parameter space and the region of interest. The two phantoms are selected to have dielectric properties respectively above and below those of the average human head, and as such will correspond to S-Parameters that bracket the region of interest. The phantoms are also of ellipsoidal shape and with dimensions to approximate an average human head.

The calibration (using the formula given above) is applied in the latent space, rather than in S-Parameter space. This is found to be far superior, which can be understood given that the space of S-Parameters is vast ($\mathbb{C}^{16 \times 16 \times 751}$), whereas the latent space is two orders of magnitude smaller ($\mathbb{R} \approx^{1000}$).

The latent space calibration is a physics-based alternative technique to transfer learning, a data-driven technique for closing the gap between simulation and reality. More specifically, since the dielectric distribution VAE 206 allows both encoding and decoding, then if a small set of real-world tuples of (S-parameter, ground-truth) is made available, then the mapping model 204 can be fine-tuned to improve its performance with real-world data. Notably, the dielectric distribution VAE 206 itself does not need to be tuned because it works in a pure image space, and the S-Compressor 208 also does not need any tuning because it is already trained with both simulation and real world data, and experiences no drop in performance with real data. Only the mapping model 220 may need to be fine-tuned.

With calibration, the overall process can be summarised as follows. For the calibration phantoms (in this example, the two calibration phantoms $Cal^1$ and $Cal^2$), their S-parameters, both as physically measured by the antenna array $$(Cal_s^1, Cal_s^2)$$

and as simulated measurements $$(Cal_t^1 \text{ and } Cal_t^2),$$

are processed by the scattering parameter compressor 208 to generate corresponding scattering parameter code, and these codes are then used to calculate the calibration factors or coefficients $\alpha$ and $\beta$. Subsequently, a set of real-world S-parameter measurements of an object of interest is then compressed by the scattering parameter compressor 208. The mapping component 204 applies the calibration coefficients $\alpha$ and $\beta$ to the scattering parameter matrix as described above to calculate corresponding calibrated scattering parameter code, which is then processed by the neural net of the mapping component 204 to generate corresponding dielectric distribution (or 'image') code, which in turn is decompressed by the dielectric distribution (or 'image') decompressor 214. As known by those skilled in the art, the decompressed code from a neural net is in the standardized form, as numerical values $\in [0,1]$, and consequently these values are scaled to generate dielectric distribution data representing a spatial distribution of at least one dielectric property (typically, relative permittivity gr).

EXAMPLES

In this section, the performance of the apparatus and process described herein is compared to that of an alternative data-driven approach referred to herein as "DeepNIS" and as described in L. Li, L. G. Wang, F. L. Teixeira, C. Liu, A. Nehorai, and T. J. Cui, *"Deepnis: Deep neural network for nonlinear electromagnetic inverse scattering,"* IEEE Transactions on Antennas and Propagation, vol. 67, no. 3, pp. 1819-1825, 2019, albeit enhanced by concatenating ten frequency channels.

Figure 10:
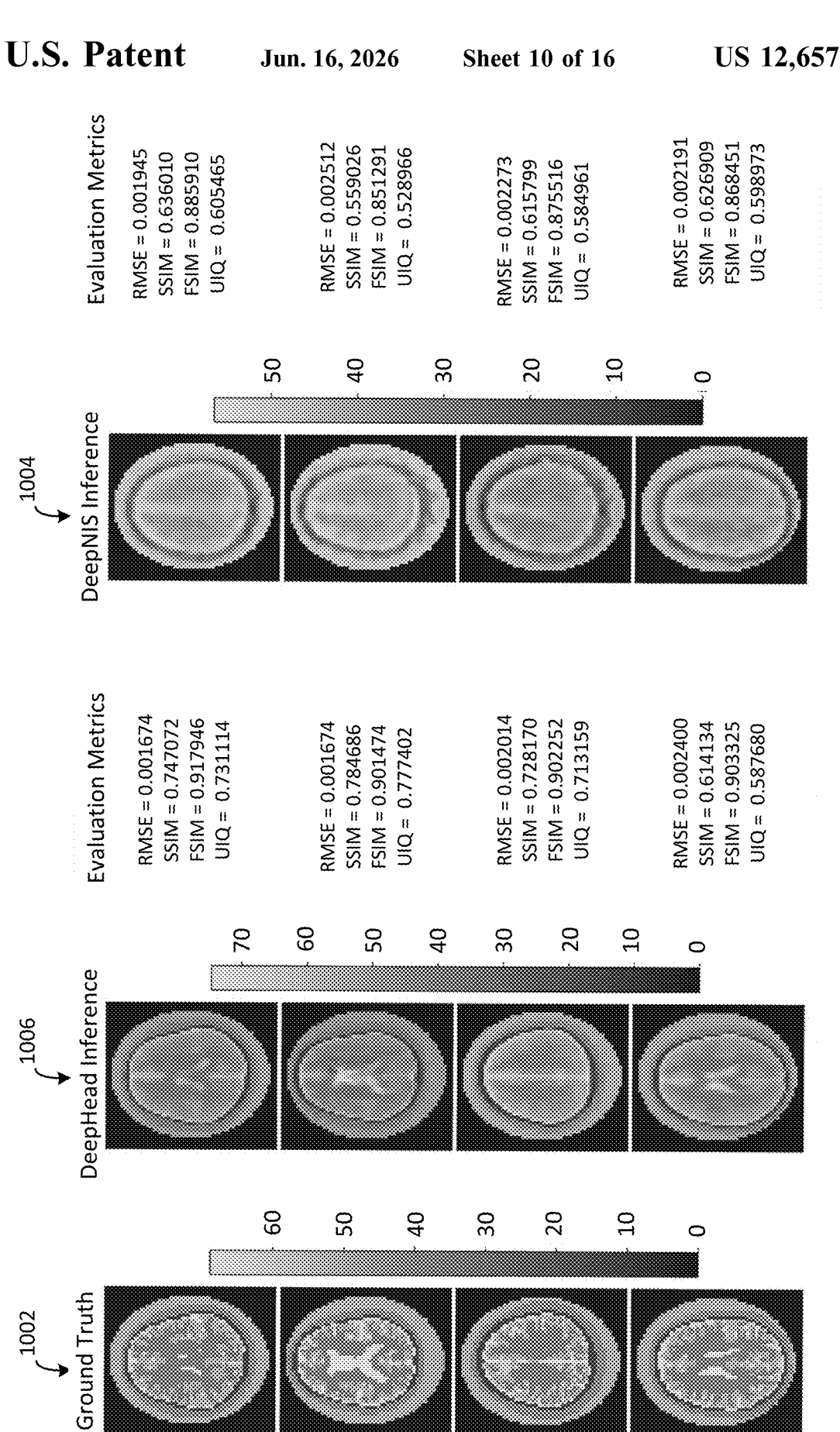
FIG. 10 shows the results of processing simulated S-parameters measurements of four simulated human heads with the apparatus and process described herein (referred to in the Figures as "DeepHead") and by the DeepNIS process (see text for details)

FIG. 10 shows the results of processing simulated S-parameter measurements of four simulated human heads with the apparatus and process described herein (referred to in the Figures as "DeepHead") and by the DeepNIS process. The four cases were selected from a reserved (for testing) 10% of the labelled data generated as described above (the other 90% of which was used to train the mapping component 204).

Compared to the ground truth images (left column of images) 1002, the DeepNIS inference images (right column of images) 1004 are blurry, and do not show significant features. Furthermore, the skull and skin layers are not resolved, but are merged into a single layer with intermediate permittivity. In contrast, the DeepHead images 1006 resolve both layers. Moreover, DeepNIS was found to be particularly prone to overfitting the simulation results, given the tiny dataset (933) involved in training, and as such the results shown can be attributed to memorization. Meanwhile, the Deephead apparatus and process use only a single layer model with no activation function, and consequently memorization is improbable.

Quantitatively, the inferences made by the two models were evaluated against the ground truth using measures of Root Mean Square Error (RMSE), Structural SIMilarity Index (SSIM), Feature-based Similarity Index (FSIM), and Universal Image Quality index (UIQ). Almost invariably, the DeepHead results exhibit less error on the RMSE scale, and higher similarity to the ground truth using the remaining metrics when compared to the DeepNIS model.

To assess real-world performance, in parallel a clinical campaign was independently conducted with 10 volunteers using a microwave imaging system that utilizes an antenna array with the same configuration as the simulations described above. As the ground truth dielectric properties for those volunteers was not available, an MRI and/or CT scan of each volunteer was obtained. The scanned slice at electromagnetic scanning time for that volunteer was estimated based on the scanning protocol. This estimated slice was extracted from the full 3D-MRI/CT scan, and was used for comparison. However, it should be noted that the resulting comparisons are strictly qualitative. The imaging modalities are different, hence a quantitative assessment of result is not possible. For example, bone (skull) appears dark, bright, or dark in MRI, CT, and electromagnetic imaging, respectively.

Figure 11:
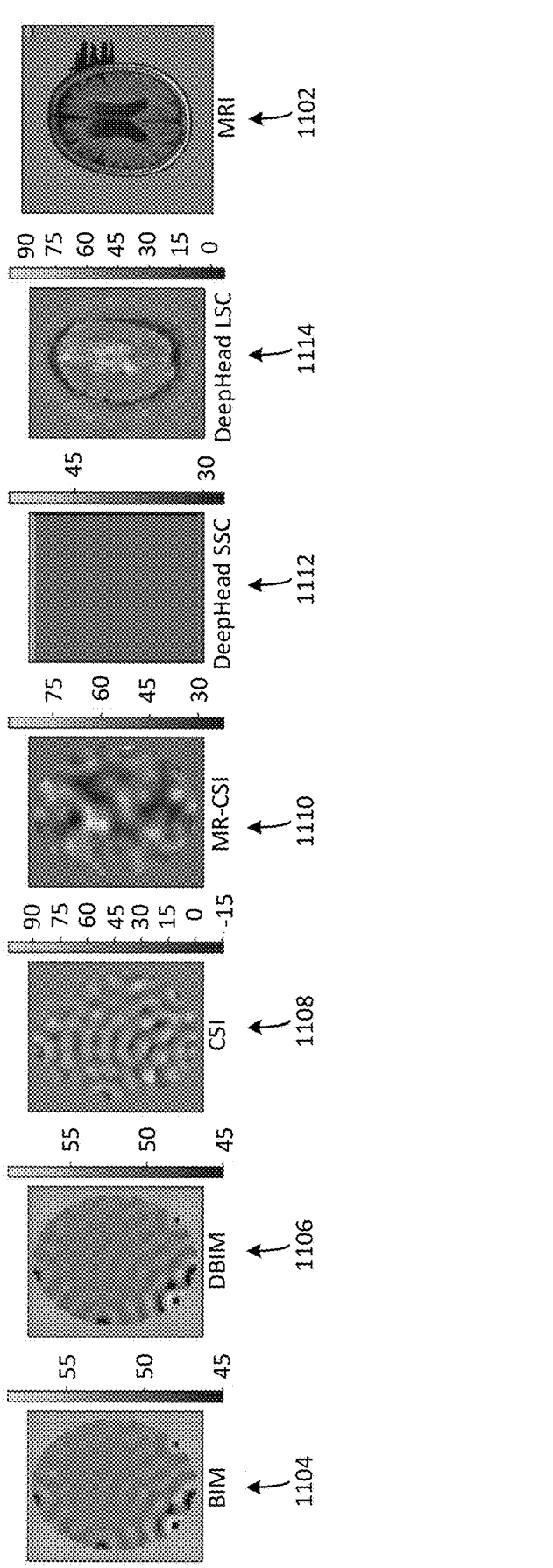
FIG. 11 is a set of seven images of the brain of a clinical case, including an MRI image (rightmost image 1102), and six corresponding microwave scattering images generated by processing S-parameter measurements with four different mainstream tomography algorithms and the DeepHead process as calibrated using S-Parameter space calibration (labelled "SSC") or latent space calibration (labelled "LSC")

FIG. 11 is a set of seven images of the brain of a clinical case, including an MRI image (rightmost image 1102), and six corresponding microwave scattering images generated by processing S-parameter measurements with four different mainstream tomography algorithms and the DeepHead process as described herein, as calibrated using S-Parameter space calibration (labelled "SSC") or latent space calibration (labelled "LSC").

The mainstream prior art tomography algorithms whose results are also shown FIG. 11 are:

(i) "BIM" 1104 (as described in Y. Yao, Y. Wang, Y. Pei, W. Zhu, and R. L. Barbour, "*Frequency domain optical imaging of absorption and scattering distributions by a born iterative method*," J. Opt. Soc. Am. A, vol. 14, no. 1, pp. 325-342, January 1997), (ii) "DBIM" 1106 (as described in W. C. Chew and Y. M. Wang, "*Reconstruction of two-dimensional permittivity distribution using the distorted born iterative method*," IEEE Transactions on Medical Imaging, vol. 9, no. 2, pp. 218-225, 1990), (iii) "CSI" 1108 (as described in P. M. van den Berg, A. L. van Broekhoven, and A. Abubakar, "*Extended contrast source inversion*," Inverse Problems, vol. 15, no. 5, pp. 1325-1344, October 1999), and (iv) "MR-CSI" 1110 (as described in Z. Hu, L. Lianlin, and L. Fang, "*A multi-frequency MRCSI algorithm with phaseless data*," Inverse Problems, vol. 25, no. 6, p. 065006, April 2009).

It can be observed by comparing the MRI image 1102 to those generated by the traditional prior art tomography solvers 1104 to 1110, that the prior art solvers predominantly produce artefacts in the form of scattered 'blobs', and do not reproduce significant features apparent from the MRI image 1102. FIG. 11 also demonstrates the advantage of using latent space calibration (image 1114 labelled "DeepHead LSC") over S-Parameter space calibration (image 1116 labelled "DeepHead SSC"), as the image 1112 generated using the latter is essentially a blank image.

Figure 12:
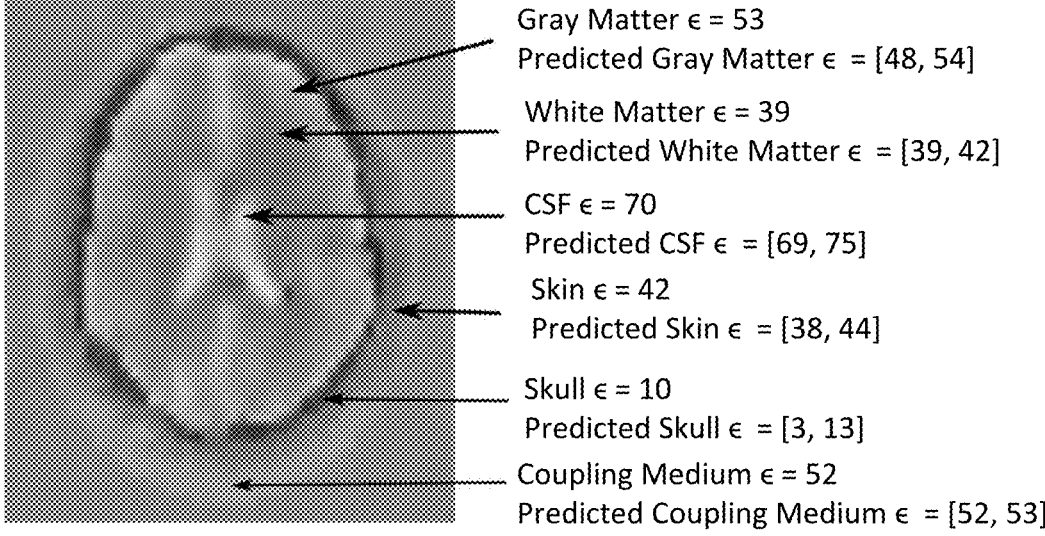
FIG. 12 is an image of a human brain generated by the apparatus and process, and showing the inferred permittivity values of the different types of brain tissue calculated by the described apparatus and process, and for comparison the corresponding actual ranges of permittivity.

Table 1 below and FIG. 12 show the inferred permittivity values of the different types of brain tissue, as calculated by the described apparatus and process, and for comparison the corresponding actual ranges of permittivity as reported at https://itis.swiss/virtual-population/tissue-properties/database/dielectric-properties. It can be seen that, for almost all tissues, the inference made is within 3% of 'ground truth' permittivity values. This is not the case for the skull, however, which itself has two different layers of bone (Cortical and Cancellous). The skull layer is the hardest as its contrast changes abruptly with respect to the adjacent layers, leading to more scattering.

TABLE 1

|  | Actual and Inferred Permittivity values of different materials within the DOI | |
| --- | --- | --- |
| Material | actual permittivity | predicted permittivity |
| Gray Matter | 53 | [48, 54] |
| White Matter | 39 | [39, 42] |
| CSF | 70 | [69, 75] |
| Skin | 42 | [38, 44] |
| Skull | 10 | [3, 13] |
| Coupling Medium | 52 | [52, 53] |

Figure 13:
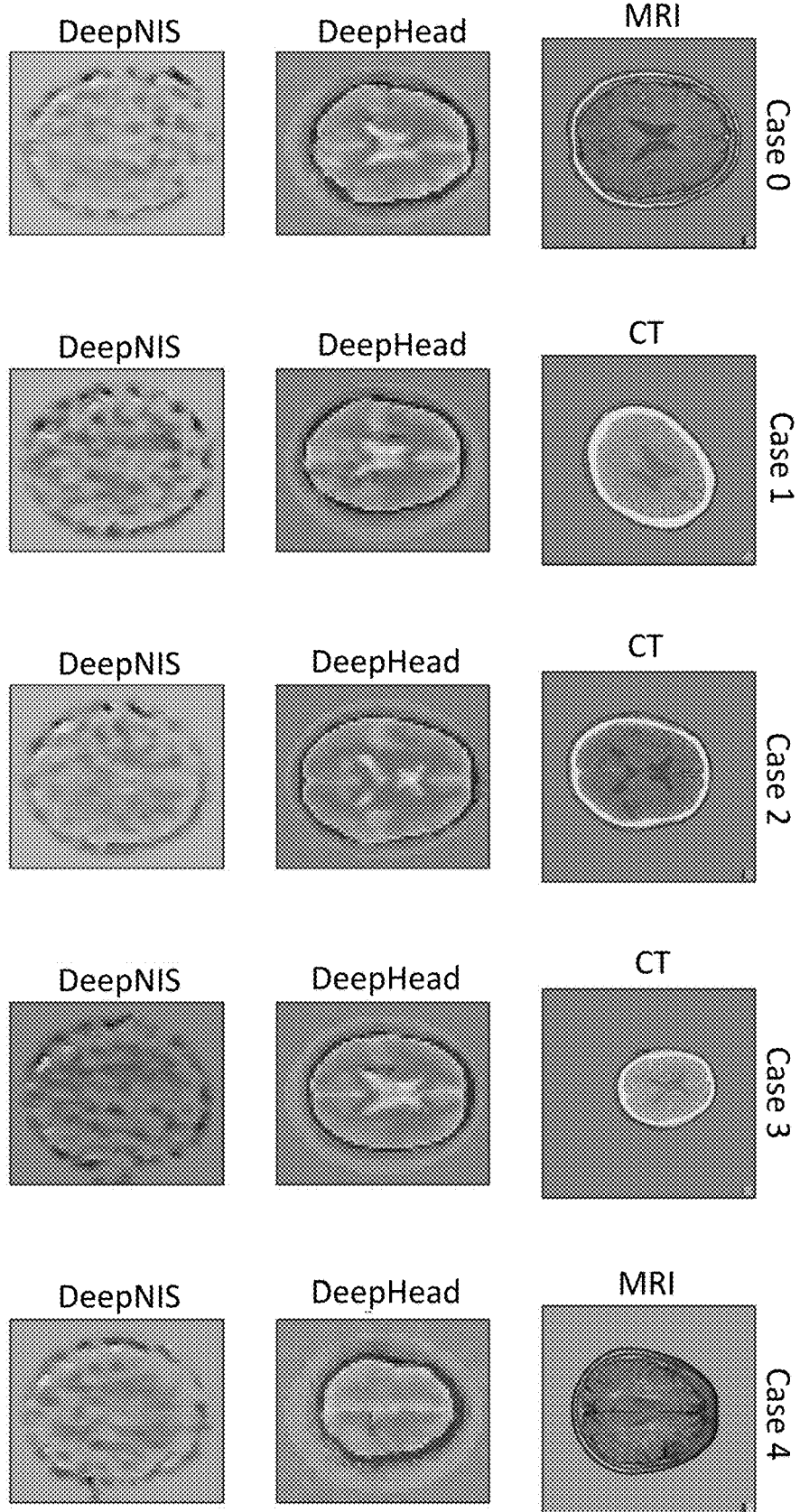
FIGS. 13 and 14 show respective sets of images of the brains of, in total, ten clinical cases, wherein for each case, a set of three images of the subject's brain is shown, consisting of a CT or MRI image (rightmost column), and a pair of microwave scattering images generated from measured S-parameters, respectively using DeepNIS (leftmost column) and DeepHead (centre column)
Figure 14:
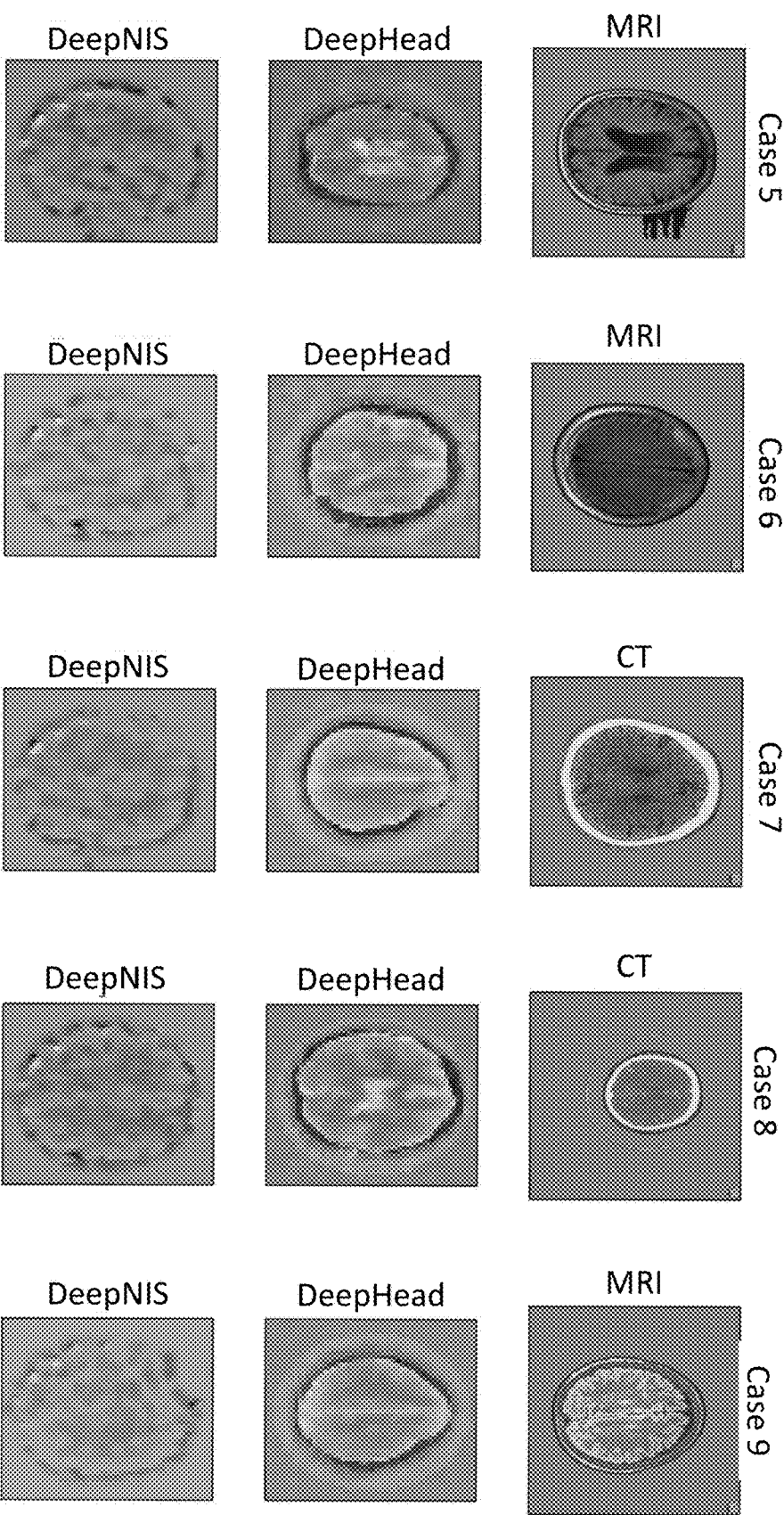

FIGS. 13 and 14 show two sets of images of the brains of, in total, ten clinical cases. For each case, a set of three images of the subject's brain is shown, consisting of a CT or MRI image (rightmost column), and a pair of microwave scattering images generated from measured S-parameters, respectively using the prior art DeepNIS process (leftmost column) and the DeepHead process described herein (centre column).

Computational Requirements

Although a forward run in a neural net typically requires about half a second on almost any typical desktop computer available today, the process described above comprises 12 neural nets, many of which are sequentially connected. In practice, the overall (wall clock) run time is around 15 seconds when processing real-world (i.e., not simulated) data where a computationally expensive latent-space calibration step is involved, although this can be reduced to less than 5 seconds if the compression of S-Parameters is parallelized. When processing simulation data, the process requires only about 1 second.

Inference Stability

The apparatus and process described herein provide stable inference, as has been quantified by performing clinical experiments as follows. For each of several different clinical cases, multiple scans of a subject's head were conducted with a period of 1 minute between consecutive scans. In the worst case, the S-Parameters exhibited stability of −40 dB. For measurements made within 1.5 seconds of one another, the achieved 'instantaneous' stability was −55 dB.

Figure 15:
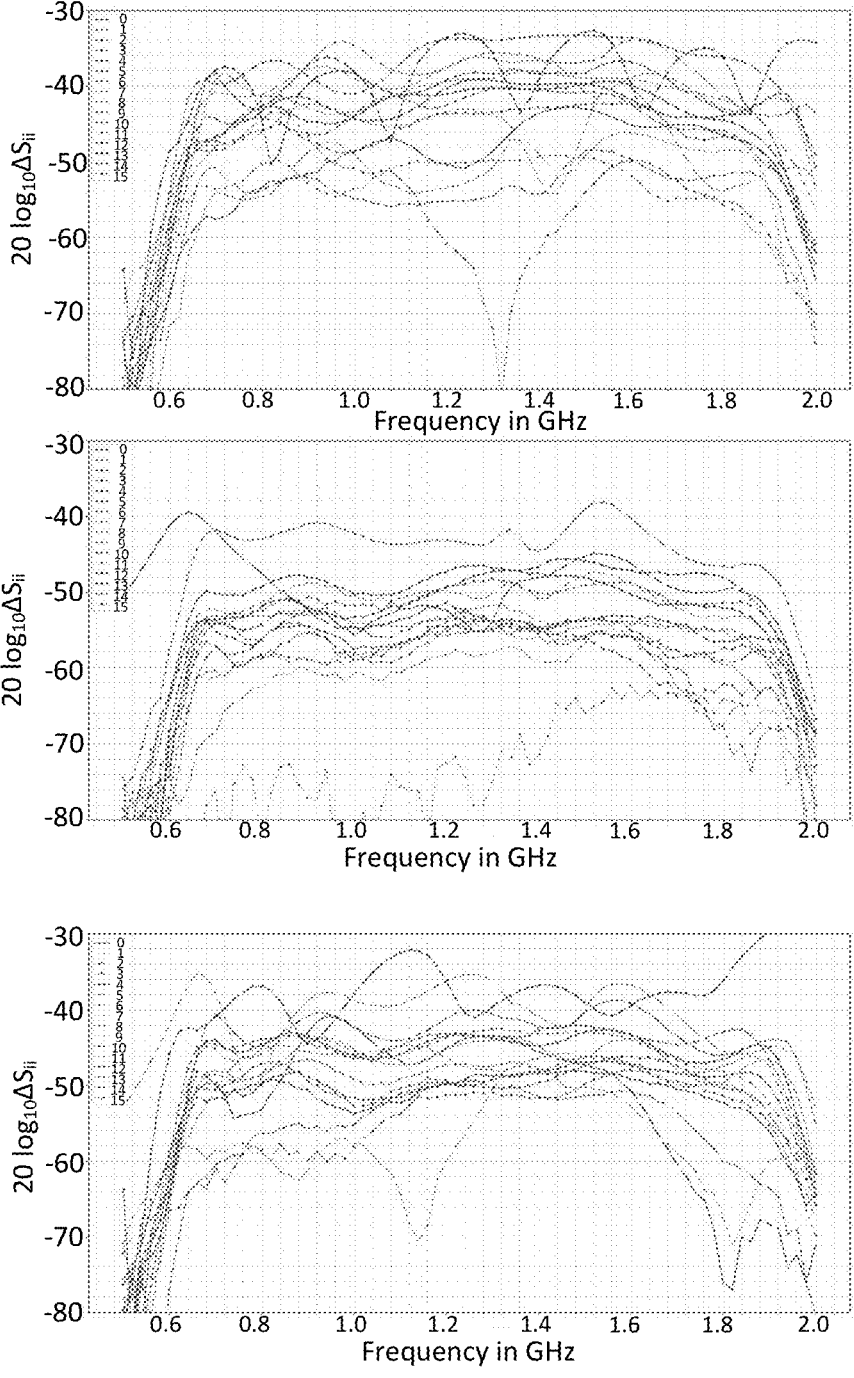
FIG. 15 is a set of three graphs of differences in repeated measurements of a reflection coefficient $S_{i,i}$, S-Parameter for three respective clinical patients.
Figure 16:
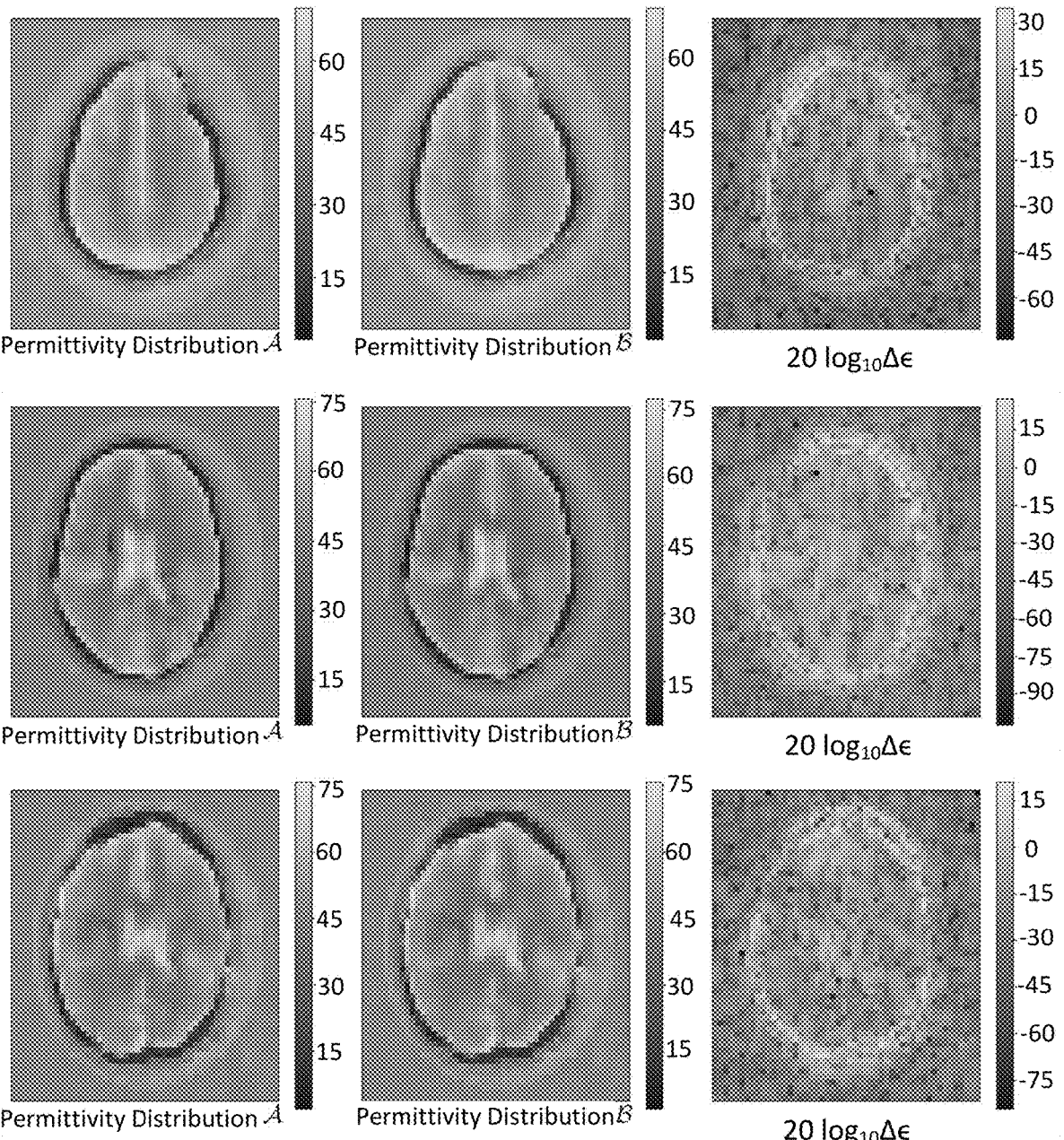
FIG. 16 includes three sets of brain images for the same three subjects of FIG. 15, with the first and second columns being images generated from consecutive measurements taken one minute apart, and the third column showing the differences between these two images, according to: $20 \log_{10} \Delta\in$, demonstrating that the inferences are quite stable.

To illustrate this further, FIG. 15 is a set of three graphs of differences between repeated measurements of a reflection coefficient $S_{i,i}$ S-Parameter for three respective clinical patients, calculated according to $20 \log_{10} \Delta S_{i,i}$. The measurements were spaced by a rest period of one minute, and the reflection coefficients $S_{i,i}$ were chosen because they were found to be the least stable of all the measured S-Parameters. FIG. 16 includes three corresponding sets of brain images for the same three subjects, with the first and second columns being images generated from consecutive measurements taken one minute apart, and the third column showing the differences between these two images, according to: $20 \log_{10} \Delta \in$. It can be seen that the inferences are stable.

It will be apparent from the above that the apparatus and process of the described embodiments implement a data-driven and stable model for inferring spatial distributions of dielectric properties in microwave imaging of human brains, a scatterer that has arbitrarily complicated dielectric distributions. The apparatus and process make full use of 'cheap' unlabelled data by learning a compression model for each of the disconnected ends of the model (i.e., S-Parameters, dielectric distributions). This is important because labelled data is scarce in many microwave imaging applications, particularly biomedical ones.

Performance-wise, despite being imperfect, the results represent a substantial advance in what has been thought to be the maximum amount of information that can be squeezed out of S-Parameters, as evidenced by the above comparisons with state-of-the-art physics-based solvers and other learned models. The results described above qualitatively approach the golden standards of MRI and CT, rather than prior art microwave imaging techniques.

Notwithstanding the excellent performance of the embodiments described herein, further improvements are being contemplated by the inventors. In particular, while training the dielectric distribution auto-encoder 206, the loss function naturally emphasises correct reconstruction of the overall shape of the head, and consequently major features such as the skull and CSF dominate the optimization, whereas subtle difference in dielectric distribution might not be represented in the resulting model 218 because they do not contribute significantly to the objective function. That said, many algorithms described in the literature can identify features or estimate the size and location of anomalies of interest by simply utilizing symmetries and the geometry of both the brain and the array itself (see, for example, A. Trakic, A. Brankovic, A. Zamani, N. Nguyen-Trong, B. Mohammed, A. Stancombe, L. Guo, K. Bialkowski, and A. Abbosh, "*Expedited stroke imaging with electromagnetic polar sensitivity encoding*," IEEE Transactions on Antennas and Propagation, vol. 68, no. 12, pp. 8072-8081, 2020, and A. Brankovic, A. Zamani, A. Trakic, K. Bialkowski, B. Mohammed, D. Cook, J. Walsham, and A. M. Abbosh, "*Unsupervised algorithm for brain anomalies localization in electromagnetic imaging*," IEEE Transactions on Computational Imaging, vol. 6, pp. 1595-1606, 2020). Thus these existing symmetry-based algorithms can be used in combination with the output of the apparatus and process described herein to provide more accurate identification of anomalies such as brain stroke, for example. Being a data-driven model, continuing improvements in neural network technology will naturally lead to embodiments with improved performance relative to the embodiments described herein.

Architecture-wise, the weakest aspect of the apparatus and process described herein is the mapping component 204 that maps compressed S parameters to image code. The mapping component 204 of the embodiment described above concatenates the S-parameters to create a 1360 long vector, and maps it to image code via a single layer neural net (purposefully chosen to avoid over-fitting). However, a more informative architecture that better reflects domain knowledge is a worthy goal. Despite the fact that the mapping component 204 operates in latent space, interpretability is not lost, and domain knowledge remains applicable because the S-Parameters signals are compressed separately. On the output side of the mapping component 204, uncorrelated latent variables for brain images are possible; for example, a VQ-VAE, as described in A. van den Oord, O. Vinyals, and K. Kavukcuoglu, "*Neural discrete representation learning*," CoRR, vol. abs/1711.00937, 2017 can be utilized to obtain meaningful latent variables.

Finer resolution simulations are desirable because less realistic simulations exert more pressure on the latent space calibrator to bridge the gap between the source and target domains, which in turn translates to a reduced likelihood of success in real-world settings. Tightly coupled to this issue is the quality of the head models themselves. Higher meshing is only useful when the model itself has high resolution. Unfortunately, there is a cubic relation between simulation time and mesh cell size.

In general, it is desirable to simulate a rich dataset that truly reflects the application of interest. A dataset with dielectric models of the human brain with targets are required to achieve higher quality results.

Additionally, the compression should be curated to maintain the features of interest. Furthermore, with ongoing progressive improvements in generative models, a 2 mm resolution output is not far-fetched. Concretely, compressing 128×128 images down to 100 dimensions is standard. Currently, the DOI is meshed with a 4 mm step size, resulting in the 58×50 images shown herein.

Finally, as described herein, the apparatus and process are only half-probabilistic (the VAE 206 is the only probabilistic component). However, the apparatus and process can be made fully probabilistic by replacing the mapping component 204 with a simple Bayesian variant. It is vital for a learning model to be able to express its uncertainty about the outcome, making it eminently suitable for applications where human lives are at stake.

Many modifications will be apparent to those skilled in the art without departing from the scope of the present invention.

The invention claimed is:

1. A computer-implemented process for electromagnetic imaging, the process comprising:

accessing scattering data representing, for each of a plurality of different electromagnetic wave energies, at least a corresponding two-dimensional array of measurements of electromagnetic wave scattering by internal features of an object, each measurement representing scattering of electromagnetic waves emitted by a corresponding antenna of an array of antennas disposed about the object, scattered within the object, and measured by a corresponding antenna of the array of antennas;

processing the scattering data with a plurality of trained neural networks to generate corresponding compressed scattering data, wherein the trained neural networks process respective subsets of the scattering data corresponding to respective different separations between the emitting and measuring antennas;

processing the compressed scattering data with a trained neural network to generate corresponding compressed dielectric distribution data; and processing the compressed dielectric distribution data with a trained decompressor to generated dielectric distribution data representing a spatial distribution of a dielectric property within the object;

wherein the trained neural networks are trained by unsupervised learning using training scattering data, the trained decompressor is trained by unsupervised learning using training dielectric distribution data representing spatial distributions of the dielectric property of objects, and the trained neural network that processes the compressed scattering data is trained by supervised learning using labelled training data.

2. A computer-implemented process of claim 1, wherein the processing of the compressed scattering data includes applying a calibration to the compressed scattering data to generate calibrated compressed scattering data, and the trained neural network generates the compressed dielectric distribution data from the calibrated compressed scattering data.

3. The computer-implemented process of claim 1, further comprising:

training the trained neural networks by unsupervised learning using the training scattering data;

training the trained decompressor by unsupervised learning using the training dielectric distribution data; and training the neural network that processes the compressed scattering data by supervised learning using the labelled training data.

4. The computer-implemented process of claim 1, wherein the trained neural networks are one-dimensional convolution compressors of a scattering data auto-encoder that includes a 'long short-term memory' ("LSTM") decompressor.

5. The computer-implemented process of claim 1, wherein the trained decompressor is a component of a variational auto-encoder.

6. The computer-implemented process of claim 1, wherein the trained neural network that processes the compressed scattering data is a single-layer neural network with no activation function.

7. A computer-readable storage medium having stored thereon executable instructions that, when executed by at least one processor, cause the at least one processor to perform the process of claim 1.

8. An apparatus for electromagnetic imaging, including components configured to perform the process of claim 1.

9. An apparatus for electromagnetic imaging, comprising:

a scattering data compressor configured to access scattering data representing, for each of a plurality of different electromagnetic wave energies, at least a corresponding two-dimensional array of measurements of electromagnetic wave scattering by internal features of an object, each said measurement representing scattering of electromagnetic waves emitted by a corresponding antenna of an array of antennas disposed about the object, scattered within the object, and measured by a corresponding antenna of the array of antennas, and to process the scattering data using a plurality of trained neural networks to generate corresponding compressed scattering data, wherein the trained neural networks process respective subsets of the scattering data corresponding to respective different separations between the emitting and measuring antennas;

a mapping component configured to process the compressed scattering data with a trained neural network to generate corresponding compressed dielectric distribution data; and a trained decompressor configured to process the compressed dielectric distribution data to generate dielectric distribution data representing a spatial distribution of a dielectric property within the object;

wherein the trained neural networks are trained neural networks of a scattering data auto-encoder configured to train the neural networks by unsupervised learning, the decompressor is a decompressor of a dielectric distribution auto-encoder configured to train the decompressor by unsupervised learning, and the trained neural network that processes the compressed scattering data is trained by supervised learning.

10. An apparatus as claimed in claim 9, wherein the mapping component is configured to apply a calibration to the compressed scattering data to generate calibrated compressed scattering data, and the trained neural is configured to generate the compressed dielectric distribution data from the calibrated compressed scattering data.

11. The apparatus of claim 9, wherein the trained neural networks of the scattering data auto-encoder are one-dimensional convolution compressors, and the scattering data auto-encoder includes a 'long short-term memory' ("LSTM") decompressor.

12. The apparatus of claim 9, wherein the dielectric distribution auto-encoder is a variational auto-encoder.

13. The apparatus of claim 9, wherein the trained neural network of the mapping component is a single-layer neural network with no activation function.

* * * * *